United States Patent
Kanter

(10) Patent No.: US 6,497,577 B2
(45) Date of Patent: Dec. 24, 2002

(54) SYSTEMS AND METHODS FOR IMPROVING EMOTIONAL AWARENESS AND SELF-MASTERY

(76) Inventor: Janet M. Kanter, 1801 Churchside La., Virginia Beach, VA (US) 23454

( * ) Notice: Subject to any disclaimer, the term of this patent is extended or adjusted under 35 U.S.C. 154(b) by 0 days.

(21) Appl. No.: 09/756,578

(22) Filed: Jan. 8, 2001

(65) Prior Publication Data

US 2002/0091307 A1 Jul. 11, 2002

(51) Int. Cl.[7] .............................................. G09G 19/00
(52) U.S. Cl. ...................................................... 434/236
(58) Field of Search ................................ 434/236, 237, 434/238, 245; 600/300

(56) References Cited

U.S. PATENT DOCUMENTS

| | | | |
|---|---|---|---|
| 4,459,114 A | 7/1984 | Barwick | |
| 4,812,126 A | 3/1989 | Gilliksen | |
| 4,931,934 A | 6/1990 | Snyder | |
| 5,696,981 A | 12/1997 | Shovers | |
| 5,790,033 A | 8/1998 | Yamamoto | |
| 5,797,839 A | 8/1998 | Herscu | |
| 5,911,581 A | 6/1999 | Reynolds et al. | |
| 5,935,060 A | 8/1999 | Iliff | |
| 5,961,332 A | 10/1999 | Joao | |
| 5,980,447 A | 11/1999 | Trudeau | |
| 5,984,368 A | 11/1999 | Cain | |
| 6,053,866 A | 4/2000 | McLeod | |
| 6,425,764 B1 * | 7/2002 | Lamson | 434/236 |

OTHER PUBLICATIONS

Gurney Williams III, "Spiritual Psychotherapy/Religion at $90 an hour?", San Francisco Chronicle; Jan. 1993.*

Douglas A. Anderson, Dan Worthen, "Exploring a Fourth Dimension : Spiritually as a Resource for the Couple Therapist", Journal of Marital and Family Therapy, 1997, vol. 23, No. 1, 3–12.*

William R. Miller, "Researching the Spiritual Dimensions of Alcohol and Other Drug Problems", Addiction, 1998.*

Gary R. Koch, "Spiritual Empowerment: A Metaphor for Counseling", Counseling and Values, Oct. 1998, vol. 43.*

EPEC, Education for Physicians on End–of life Care, Participant's Handbook, Module 2, Communicating Bad News, EPEC Project, The Robert Wood Johnson Foundation, 1999.*

U.S. Copyright Registration TXU–729–355; A Spiritual Needs Theory; Janet M. Kanter; Jun. 21, 1999.

* cited by examiner

Primary Examiner—John Edmund Rovnak
(74) Attorney, Agent, or Firm—Kaufman & Canoles

(57) ABSTRACT

This invention provides various systems and methods for providing an individual with improved emotional awareness and self-mastery. The systems and methods allow an individual to recall a situation in which the he or she experienced negative emotions. Then, the individual is able to analyze the recalled situation to identify specific negative emotions (specifically "flight" or "fight" emotions) experienced during the particular situation. Once the individual has identified specific negative emotions that were experienced during the particular situation, the systems and methods of this invention correlate each identified emotion with an underlying spiritual need. When the appropriate spiritual need(s) have been identified, the systems and methods of this invention identify at least one antidote to the spiritual need(s). The antidote(s) are then relayed to the individual for personal application. In this manner, an individual can evaluate the negative emotion(s) experienced during a particular situation and receive guidance as to how he or she can cultivate virtuous behavior that will overcome the negative emotions.

25 Claims, 6 Drawing Sheets

|  | NEGATIVE EMOTION | SPIRITUAL NEED | ANTIDOTE |
|---|---|---|---|
| Fight Emotions Rooted in Desire to Seek Power | Pride | Community | Humility |
|  | Extreme Desire | Honor | Respect |
|  | Anger / Frustration / Lashing Out | Love | Patience |
|  | Extreme Need for Pleasure | Joy | Self Discipline |
|  | Unwilling to Accept Responsibility | Life Lessons | Responsibility |
|  | Complaining | Life Work | Charity |
|  | Envy / Jealousy / Resentment | Faith | Trust in Divine |
| Flight Emotions Rooted in Desire to "Vent Off" Power | Lonely | Community | Friendship |
|  | Guilt / Shame | Honor | Courage |
|  | Hurt Feelings / Loss | Love | Compassion |
|  | Blue / Down | Joy | Present Living |
|  | Hopeless / Helpless / Victimized | Life Lessons | Responsibility |
|  | Dissatisfied / Worthless | Life Work | Perseverance |
|  | Anxious / Worried / Stressed | Faith | Trust in Divine |

Fig. 1

SYSTEMS AND METHODS FOR IMPROVING EMOTIONAL AWARENESS AND SELF-MASTERY

BACKGROUND OF THE INVENTION

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

1. Field of the Invention

This invention relates generally to systems and methods for analyzing emotions and promoting healthy emotional habits. The invention is applicable within the fields of emotional intelligence and/or health promotion and disease prevention.

2. Description of Related Art

Generally, there are two views of medicine and healthcare, an allopathic approach, and a holistic approach. Allopathic is a term applied to a system of therapeutics in which diseases are treated by producing a condition incompatible with or antagonistic to the condition to be cured or alleviated. Typically, an allopathic system focuses on the identification and cure of disease.

The allopathic approach is generally associated with Western philosophy and approaches medicine with a mechanistic approach based on a reductionist model rooted in scientifically based empirical data. This approach currently dominates the attitudes of physicians toward health and illness. Thus, allopathic medicine, as it is researched and practiced today, is deeply rooted in critical scrutiny and every theory, treatment, and medicine, is rigorously tested, evaluated, and scrutinized, before it is accepted as legitimate.

Although some aspects of the allopathic approach can be traced to Socrates, Plato, and Aristotle, the allopathic (or biomedical) model began in Europe with the Scientific Revolution of the 1500's. This approach emphasizes the study of the sciences as a basis for medical training. Therefore, the allopathic model seeks to understand something or predict an outcome through questions that are asked about a subject.

Based on this widely accepted philosophical view, western medicine considers the mind and the body to be separate and fundamentally different. Thus, the allopathic model leads to an ultimate separation of the mind from the body. Furthermore, allopathic medical treatment attempts to construct a completely scientific description of nature in which there is absolute certainty. In this manner, the allopathic model attempts to predict and control diseases.

Allopathic medicine tends to view the human body as a machine that is capable of being analyzed and understood in terms of the arrangement and functioning of its parts. Diseases are viewed as a malfunctioning, on a cellular or molecular level, of the biological mechanisms that enable the machine to operate. Thus, a doctor's role is to intervene, either physically or chemically, to correct the malfunctioning of a specific mechanism. In essence, an unhealthy person is likened to a well-made clock whose parts were not functioning properly.

The reductionist model states that a complex phenomena can be understood by reducing the phenomena to its basic building blocks and identifying the mechanisms with which the phenomena interacts. In allopathic medicine, the basic building blocks include organs, tissues, cells, Deoxyribonucleic Acid (DNA), etc.

Empiricism is the principle that the practice of medicine is based upon practical experience rather than theory. The empirical method is used when scientists make experiments and draw conclusions from data collected from the experiments. In allopathic medicine, the empirical method is used to test and research, for example, pharmaceutical products, treatments, procedures, and DNA, in hopes of providing proof or verification by means of observation or experiment.

The use of the above-described allopathic model has produced dramatic improvements in areas such as nutrition, hygiene, treatment of environmental and infectious diseases, and trauma management. For example, the acute infectious diseases that plagued Europe and North America in the nineteenth century and that are still the major killers in the Third World today have been replaced in the industrialized countries by illnesses that are no longer associated with poverty and deficient living conditions.

However, the current diseases of industrialized countries are diseases of affluence, which are primarily chronic and degenerative diseases, such as heart disease, cancer, and diabetes. These diseases are caused by (or closely associated with) lifestyle and behavior problems such as stressful lifestyles, rich diets, drug abuse, sedentary living, and the environmental pollution that is characteristic of modern life.

Although the allopathic model has been extremely successful in certain realms, it nevertheless has severe limitations. For example, the allopathic model fails to consider certain behavioral, mental, and spiritual aspects of disease and illness.

Thus, the second predominant view of medicine and healthcare is the holistic approach. Holistic is a term applied to a system of therapeutics that emphasizes the organic or functional relation between parts and the whole. Typically, a holistic system assumes that a person constitutes a single biological, psychological, and social unity that includes physical, nutritional, mental, emotional environmental, social, spiritual, and lifestyle aspects. Thus, diseases can be effectively treated only when the interrelationship between the mind, the body, and the spirit are considered.

The holistic model includes a number of factors, such as, for example, dealing with the root cause of an illness, increasing patient involvement in the treatment process, and viewing patients as wholly integrated systems of mind, body and spirit.

The holistic model has come to include natural healing, alternative medicine, and complementary medicine. Natural healing usually refers to the use of physical healing techniques that are not accepted by allopathic medical practitioners to cure disease and/or illness.

When these holistic principles are applied by a healthcare practitioner, it is usually called holistic medicine. Holistic healthcare practitioners attempt to use a person's symptom (s) as a guide to find a root cause of a disease or illness. Then, a form of treatment is selected that utilizes and complements the person's natural healing system.

Often, holistic medicine is called alternative medicine. The term alternative medicine generally refers to techniques that are not accepted by allopathic medical practitioners. These techniques include, for example, non-invasive, non-pharmaceutical techniques, such as medical herbalism, acupuncture, chiropractic therapy, massage therapy, naturopathy, homeopathy, Reiki, and the like. The precise definition of alternative medicine is constantly changing as new techniques are developed or accepted by allopathic medical practitioners. Alternative medicine is most often associated with specific techniques that encourage healing and not with techniques for adjusting the person's lifestyle habits.

The term complementary medicine (or "wholistic" medicine) is often used by allopathic medical practitioners to describe the use of alternative medical techniques in conjunction with allopathic medical treatments. Typically, in complementary medicine, the alternative medical techniques are used to supplement the primary allopathic medical treatments. Complementary medicine often proposes that properly chosen holistic healing techniques can heal both acute and chronic illnesses.

Since the 1970's, healthcare consumers have become increasingly dissatisfied with the allopathic, scientifically based, medical system. Healthcare consumers have become increasingly dissatisfied with the rising cost of allopathic medicine, the lack of availability of healthcare providers, and our "high tech" approach to healing. Furthermore, because healthcare consumers are no longer preoccupied with survival needs and acute infections, they desire a higher quality of life and treatment for chronic illness. Thus, healthcare consumers are seeking services that are health and wellness focused rather than disease treatment based.

As a result, we are currently experiencing a sociologic shift of paradigm in healthcare. Many healthcare consumers are, either consciously or unconsciously, searching for a form of medicine that honors the mind (the cognitive functions that mediate limbic activity and physiologic or action responses), the body (the endocrine, neurologic, immune, and cognitive processing systems), and the spirit (that which lies beyond the senses). People are demanding a change in healthcare services because they desire services that respect their mind, body, and spirit.

Healthcare consumers are beginning to accept personal responsibility for their health, are becoming increasingly more aware of research in alternative therapies, and are utilizing these therapies in a self-directed manner. Healthcare consumers are seeking more effective and affordable remedies for ailments, natural untainted foods, and more sensitive, respectful healthcare practitioners.

Various systems and/or methods have been developed that allow users to access allopathic medical diagnosis advice via a computerized network. For example, U.S. Pat. No. 5,935,060 to Iliff discloses a system and method for providing computerized, knowledge-based medical diagnostic advice. The Iliff system provides medical advice over a network or a stand-alone mode of a computer. To diagnose a health problem of a patient, medical knowledge is organized into a list of the diseases to be considered. Each disease on the disease list includes a list of symptoms that is checked in a patient. Each symptom on the symptom list is then further described as a response to a list of one or more questions asked of the patient about the symptom. When a patient requires diagnosis, the responses of the patient are analyzed and converted into symptoms, the symptoms are accumulated into diseases, and the diseases are selected and reported as a diagnosis.

Likewise, U.S. Pat. No. 6,053,866 to McLeod discloses a method of facilitating diagnosis of a psychiatric disorder in a patient. The McLeod method provides the patient with one or more questions relating to symptoms of one or more psychiatric disorders, records the patient's answers to the question(s), and establishes a preliminary disorder indication based on the answers provided by the patient.

Several systems and/or methods have been developed in an effort to combine the predictability and reproducibility of the allopathic, scientifically based, medical model with the total wellness focus of the holistic model. For example, U.S. Pat. No. 5,797,839 to Herscu discloses a system and method for assisting a homeopathic healthcare provider in the diagnosis and selection of treatments for a patient. The Herseu system includes a computer that stores information related to symptoms and remedies for the symptoms. As the homeopath enters symptoms, a program groups the symptoms into segments and uses the segments to select remedies for the symptoms from stored information.

SUMMARY OF THE INVENTION

In recent years, scientific studies have emerged to support the prospect that negative emotions have a detrimental effect on physical as well as mental health. Although known systems and methods attempt to combine the predictability and reproducibility of the allopathic, scientifically-based, medical model with the total wellness focus of the holistic model, the known systems and methods fail to adequately address the interrelation between the mind, the body, and the spirit. While current healthcare systems focus primarily on disease treatment, acute interventions, and curative medical techniques, they overlook a primary component of health and wellbeing which is "how a person feels emotionally".

For example, known systems and methods fail to account for the impact of emotions, particularly negative emotions, on the mind, the body, and the spirit. Currently, allopathic healthcare providers refer patients to psychiatry, social services, or clergy, to address psychosocial or spiritual matters. Although these services are helpful, they do not fulfill the patient's request for treatments that are not only health and wellness focused, but also address, respect, and balance the patient's mind, body, and spirit as an integrated whole.

Even among healthcare systems with theoretical frameworks for describing the need for balance to achieve mind, body, and spirit health, spiritual health is not fully described. Furthermore, known methods fail to provide healthcare providers or patients with the proper tools to adequately analyze, correctly diagnose, and ultimately provide an antidote for negative emotions.

Thus, known treatments fail to adequately address the view that emotions are the part of the human being that serve as the connection between the mind, the body, and the spirit. One of the most frustrating experiences in life is for a person to have worked to gain insight into 'what I am feeling' and 'why I feel the way I do' but continue to be unable to discover what he/she 'needs to do' to resolve the unpleasant feelings.

Thus, there appears to be a linear relationship between the mind, which is the interpreter of life, the body, which is the manifestation of life, the spirit, which is the source of life, and the emotions, which are the mechanism that connects the mind, the body, and the spirit. Furthermore, emotional health is a dynamic state because positive emotions and negative emotions exist on a spectrum. The more positive and the fewer negative emotions a person experiences, the higher level of physical, mental, spiritual, and emotional health the person possesses.

Additionally, overuse of the human survival mechanism called the "fight or flight response" is the source of poor physical, mental, spiritual, and emotional health. However, because human beings possess the capacity to cognitively override the "fight or flight" response, addressing overuse of the "fight or flight" response improves physical, mental, spiritual, and emotional health.

Attaining improved physical, mental, spiritual, and emotional health is an individual responsibility that requires the cognitive processing of unhealthy emotions. Unfortunately, one must first be able to isolate and identify the unhealthy emotions before they can be cognitively processed.

Once the unhealthy emotions are isolated and identified, they can be correlated to deficient spiritual needs in the person's life. Deficient or unmet spiritual needs ultimately lead to low levels of physical, mental, spiritual, and emotional health. Therefore, having a high number of satisfied spiritual needs ultimately leads to higher levels of physical, mental, spiritual, and emotional health.

Fortunately, virtuous behaviors are antidotes to unmet spiritual needs and becoming aware of the proper virtuous behaviors to cultivate as a "treatment" against deficient spiritual needs serves to assist in the cognitive processes necessary to attain higher levels of physical, mental, spiritual, and emotional health.

Accordingly, this invention provides systems and methods that provide health services that honor a patient's mind, body, and spirit. The systems and methods of this invention help to define physical, mental, emotional, and spiritual health in the absence of physical illness and assist a user in developing a balanced, wholistic (mind, body, and spirit), view of health and healing through the cognitive processing of negative emotions.

The various systems and methods of this invention assist an individual's cognitive processes to foster greater emotional and spiritual health by identifying negative emotion(s) and filling associated spiritual needs resulting in a decreased experience of negative emotion and an improvement of both emotional and spiritual health. Thus, the presentation of a negative emotion is likened to a symptom, a spiritual need is likened to a diagnosis, and an antidote (virtuous behaviors) is likened to a treatment.

It should be understood that the philosophy embodied in the systems and methods of this invention was developed using principles found in psychology, physiology of emotions, and world religions. As described in this invention, the relationships between these principles are defined as "The Spiritual Needs Theory". The Spiritual Needs Theory is built upon four main principles. These principles are 1) emotions are the key element in mental, physical, emotional, and spiritual health, 2) definitions for emotional and spiritual health are depicted as spectrums, 3) negative emotions are the symptoms of unmet spiritual needs, and 4) all individuals are personally responsible to identify and to meet their own needs.

Emotions are the part of the human being that serve as the connection between the mind, the body, and the spirit. Emotions are the measuring stick for mental and/or emotional health, like a flag that leads to the identification of unmet needs. Theories in neurophysiology explain the role that emotions play in the connection between the mind and the body. It is thought that emotions originate in the limbic system of the brain and impact the body through the endocrine system (glands and hormones), the neurologic system (the body's electrical system), the immune system (the body's system for fighting disease), and the cognitive processing system (the system that determines the actions that one takes).

Physiologists have determined that the hypothalamus is required for outward expression of emotion, particularly the visceral components (the experience of feeling emotion in the body) and that cortex involvement is necessary for directed emotional expression (such as an attack on an object).

The emerging field of psychophysiology has produced a number of quality studies that measure the physiologic impact of emotions on the body. Currently, experiments are being conducted on techniques such as biofeedback which are tools used to cognitively control the impact of one's emotions on the body.

Thus, the human being is a "whole" and the mind, the body, and the spirit are not reduced elements, but act and interact as a single, integrated system. Therefore, just as emotions are the connection between the mind and the body, emotions are also the connection between the mind and the spirit. As a result, mind, body, and spirit balance, and consequently health, is connected, regulated, and controlled by emotions.

A person's expression of emotions, such as, for example, rage or pleasure, is controlled by the body's limbic system. The limbic system is composed of the hypothalamus, the thalamus, the anagdala, and several fiber tracts connecting these areas. Scientific studies have shown that stimulation of the amygdala produces aggressive responses, while destruction of the amygdala causes, for example, violent animals to exhibit hyper-sexuality and no fear of objects that formerly produced fear. Thus, physiologists believe that the amygdala contains the "fight or flight" response. The "fight or flight" response is the function of the sympathetic nervous system that is responsible for mobilizing the body in times of stress. A "fight" response is typically characterized by reactions that are power seeking, wanting, and selfishness; while a "flight" response is typically characterized by reactions that include the giving up of power, passiveness, and victimization.

Negative emotional reactions (emotional responses that stem from the "fight or flight" response) are dictated by habits in a person's personality and have movement like the swing of an unstable pendulum. Thus, in a moment one's emotions can "swing" from a "fight" response to a "flight" response and back again.

All human emotions fall within a spectrum that ranges from all experiences manifesting positive, healthy emotions, such as, for example, love, happiness, bliss, relief, rapture, satisfaction, peaceful, and the like (identified as a state of "non-duality") to all experiences manifesting negative, unhealthy emotions, such as, for example, fear, anxiety, humiliation, guilt, shame, depression, apprehension, terror, helplessness, anger, outrage, resentment, exasperation, wanting, indignation, and the like (identified by a "fight" or "flight" response).

It should be understood that the term non-duality refers to perceptions and feeling of connectedness and unity that occurs in the absence of fear and separation. Non-duality is not the experience of me vs. you, but the experience of us. The systems and methods of this invention realize that the more positive emotions a person experiences and the fewer negative emotions a person experiences, the greater emotional health that person possesses.

Maslow's needs theory states that individuals have a basic level of physiologic needs that must be met to ensure survival and the higher level of needs that must be met to ensure happiness and satisfaction with life. Thus, in keeping with Maslow's "Hierarchy of Needs", an individual's emotions and responses are based on need driven behavior. Negative emotions are a result of need driven behavior and stem from unmet or deficient spiritual needs. Not only must these spiritual needs be met to ensure happiness and satisfaction with life, these spiritual needs, which are manifest as negative emotion(s), must be met to ensure survival.

Although negative emotions may not have an immediate impact on survival, negative emotions have long-term consequences on health through the mind/body connection (endocrine, neurologic, immune, and cognitive systems). Furthermore, the cognitive processing of negative emotions leads to behavioral survival risks such as violence, war, or suicide.

As shown in FIG. 1, the systems and methods of this invention identify two general categories of negative emotions. The first general category includes negative emotions rooted in a desire to seek power (the "fight" response of the physiologic "fight or flight response" mechanism). The second general category includes negative emotions rooted in the desire to "vent off" or "be rid of" power for self-preservation (the "flight" responses of the physiologic "fight or flight response" mechanism). These two general categories are further broken down into fourteen subcategories of negative emotions that correlate directly to seven spiritual needs. Within the subcategories of negative emotions there are seven subcategories of emotions that are rooted in a desire to seek power and seven subcategories of emotions that are rooted in a desire to "vent off" power. The power-seeking negative emotions are grouped into the following subcategories; pride, extreme desire, anger/frustration/lashing out, extreme need for pleasure, unwillingness to accept responsibility, complaining, and envy/jealousy/resentment. The "venting off" negative emotions are grouped into the following subcategories; lonely, guilt/shame, hurt feelings/loss, blue/down, hopeless/helpless/victimized, dissatisfied/worthless, and anxiousness/worry/stress.

The systems and methods of this invention utilize seven basic needs as a "diagnosis" for negative emotions. These seven basic needs are termed "spiritual needs" because they are human needs that have been synthesized from of ideas and commonalities among the six major religions of the world and are beyond a person's needs for immediate physical survival. As shown in FIG. 1, the seven spiritual needs include community, honor, love, joy, life lessons, life work, and faith.

The spiritual need for community is a need for people in each person's life to provide love and support. The spiritual need for community is the need to have reciprocal relationships in which one is provided, and provides love and support for those in his/her community. Support is being able to turn to someone for physical, emotional, and/or spiritual assistance when it is needed. Physical support is, for example, having someone who is willing to help with physical problems or setbacks. Emotional support is having someone who is willing to help you process through what you are feeling. Spiritual support is having someone who will understand, respect and support your spiritual beliefs and is available to discuss and process spiritual issues.

Generally, a community is perceived as a neighborhood, ethnic group, or religious affiliation. Community in the context of spiritual needs may include, for example, family or cultural ties, individuals such as friends, coworkers, neighbors, and the like. Ultimately, a community consists of any number of people who recognize your goodness and lovingly offer direction and support in a trusting, reciprocal relationship that provides a mutual experience of love and support.

The spiritual need for honor is the need to feel honorable and express honorable behavior towards others. The feeling that comes with having met one's need for honor is a feeling of being respected, held with esteem, and treated with dignity. The expression of the spiritual need for honor is to have noble intentions and be respectful towards others. Having an attitude of noble intentions is done without obligation and conveys a feeling of alliance and respect. Being respectful towards others is manifested through moral behavior.

Love is most frequently thought of as an emotion. Love is an interesting phenomenon in that if you have ever experienced love, it needs no definition. If you have not experienced love, it cannot be defined. The spiritual need for love is the need to both give and receive love. The feeling that comes from being loved is characterized by the receiving of affection, caring, concern, and being treated with warmth and kindness. Giving of one's love is characterized by the giving of your attention, affection, caring, concern, and warm responses.

The spiritual need for joy is the need to feel buoyant emotions, light heartedness, excitement, delight, playfulness, or simply having fun in your life. The spiritual need for joy is about balancing the serious or difficult aspects of life with lighthearted experiences in life. Joy may well be the one experience human beings want the most and find most illusive. Some of us deny ourselves the joy we need out of guilt, work ethic, lack of time, or merely not having the frame of mind required to recognize and engage in joyful experiences. Others seek transient pleasures that provide short-term feelings of pleasure but require a constant renewal of pleasurable experiences to maintain. Joy requires a shift in perception that results from learning how to "live in the moment". The result of fulfilling your need for joy is the experience of happiness.

The spiritual need for life lessons is a point of view that sees difficulties in one's life as an opportunity to learn, grow, mature, evolve, improve, or heal. An appropriate perception of life lessons requires a view that difficulties are a normal part of life and difficult experiences provide an opportunity to learn and grow. The result of developing the proper attitude is a greater experience of the positive emotion of hope.

The spiritual need for life work is each person's need to use his/her gifts and talents. When using gifts and talents, you will experience the feeling that you have made an important contribution, that you are needed, wanted, valued, and appreciated. The result of using you gifts and talents is a feeling of satisfaction and meaning in life.

The spiritual need for faith is the need to trust in the Divine (trust in God). This trust manifests itself in the attitude (or belief) that; 'God has a greater plan'. We may not be able to see or understand why something is happening but we have faith that there is a Divine reason for everything. The result of having faith in the Divine is a feeling of peace.

As further shown in FIG. 1, each of the fourteen negative emotions described above corresponds to one of the seven spiritual needs. It should be understood that each of the seven spiritual needs actually corresponds to one of the negative emotions that is rooted in a desire to "vent off" power, and one of the negative emotions that is rooted in a desire to seek power.

Thus, for example, if an individual is experiencing the negative emotion of loneliness or pride, the corresponding spiritual need is community. If the individual is experiencing the negative emotion of guilt or extreme desire, the corresponding spiritual need is honor. If the individual is experiencing feelings of loss or anger, the corresponding spiritual need is love. If the he or she is feeling down or feels an extreme need for pleasure, the corresponding spiritual need is joy. If the individual is experiencing the negative emotion of hopelessness or an unwillingness to accept responsibility, the corresponding spiritual need is life lessons. If the individual is experiencing the negative emotion of dissatisfaction or is complaining, the corresponding spiritual need is life work. Finally, if the individual is experiencing the negative emotion of anxiety or envy, the corresponding spiritual need is faith.

Finally, the systems and methods of this invention utilize virtuous behaviors, as shown in FIG. 1, as antidotes, or more specifically, "emotional antidotes", for the identified spiritual needs, and ultimately the negative emotions. The antidotes include friendship, courage, compassion, present living, responsibility, perseverance, trust in Divine, humility, respect, patience, self discipline, and charity.

The antidotes to the categories of negative emotions function much the same as antidotes in medicine. A "medical antidote" serves to remedy or counteract a poison. Similarly, the "emotional antidotes" are virtuous behaviors or reactions that, when utilized, serve to counteract the experience of negative emotions. The following is a brief summery of the essence of the "emotional antidotes" presented in this invention.

The antidote to the emotions in the category of lonely is friendship. The antidote of friendship is to consciously seek out, promote and develop reciprocal relationships that serve to meet one's need to be supported by a community.

The antidote to the emotions in the category of guilt/shame is courage. Courage is a state or quality of mind or spirit that enable one to face danger or oppression with confidence with resolution and bravery. Courage means facing one's fears and taking a stand in a conflict. Courage is acting bravely when one does not feel brave.

Courage is a developmental gift that comes from confronting one's own most frightening "dragons". With courage comes freedom from the bondage of ones fears. The antidote of courage does not mean one will no longer fear, it means that one can learn to "make friends with fear" by long acquaintance. Instead of being immobilized by fear, one can begin to see that fear can be an invitation to growth and a motivation for change.

The antidote to the emotions in the category of Loss/hurt feelings is compassion. To have compassion requires that one consciously try to see and/or understand a point of view other than one's own. Compassion requires an understanding that everyone has their own individual path and a willingness to honor what people need to experience in order to grow. It does not matter whether a hurtful event was intentional or unintentional, it matters how one responds to the situation. Consciously choosing to respond to hurtful situations with compassion is a reflection of maturity. Much as a parent who sees a child lashing out as a child who needs love or guidance, having compassion for those who have hurt us fosters love, relationship, and understanding.

The antidote to the emotions in the category of blue/down is to live in the moment. Living in the moment happens when one has gained enough life experience to be able to view life as a continuum of happy and sad (good and bad) experiences. A statement that best describes this emotion is "taking the good with the bad". Living in the moment is about being conscious of every moment, understanding that suffering is part of life, and savoring the moments that bring us joy.

The antidote to the emotions in the category of hopeless/helpless/victim is responsibility. The antidote of responsibility means to be answerable and accountable for oneself, one's actions, and one's life. One's ability to take responsibility for oneself is a sign of maturity. Irresponsible behavior is equated with immature behavior. Becoming responsible for oneself leads to maturity and maturity is the path to full ownership of one's power.

In other words, responsible persons are mature people who have the power to take charge of themselves and their conduct. Responsible persons own their actions, own up to their actions, and answer for their actions. One's ability to be responsible comes through practice and experience.

As an individual identifies ways to deal with the cause of suffering, he/she learns that they do not have to be at the mercy of evil, illness, patriarchy, capitalism, and the like. Hence, the antidote of responsibility provides the experience of hope. When one is able to view himself or herself as having enough power to impact their experience, they have hope for something better. Hope keeps people alive in any number of abusive or dehumanizing situations. What keeps people from plunging into the depths of despair is knowing that if change is possible, there is hope for something better.

The antidote to the emotions in the category of dissatisfied/worthless is perseverance. The antidote of perseverance means to adhere to a course of action, belief, or purpose, without giving way. The task that one is persevering to achieve is to "know oneself" and make proper "boundaries". It is essential to create proper boundaries so that we can see that difference between ourselves and others. Boundaries help us to know ourselves and what we want. Boundaries also help us to stop compromising to please others. With the creation of these boundaries, it becomes possible to both honor others and do what we need to do for ourselves. The antidote to the emotions in the category of dissatisfied/worthless is to discover and use one's unique gifts, talents, and experiences. The skill of perseverance is necessary in achieving this goal.

The antidote to the emotions in the category of anxious/worried/stressed is to trust in Divine. The emotion that results form trusting in Divine (or trusting in God) can be elicited through statements such as; "God will not give me more than I can handle", and "Everything for a reason". Trust in Divine does not mean that one is not responsible for their lives. Trust in Divine means that we may not be able to see why something has happened, but God always has our best interest in mind.

The antidote to the emotions in the category of pride is humility. To have humility is to have an attitude or spirit of modesty and to show respect for others. Humility that reflects another person's value and worth builds trusting relationships and altruism.

Humility is different from humiliation. Humiliation is an emotional state that arises from the experience of having been humiliated or shamed. Humility is a quality of personality in which a person is able to view oneself as being neither worth more than nor less than another person. Pride separates us from community while humility builds community and serves to fill one's spiritual need for the support of a community.

The antidote to the emotions in the category of extreme desire/greed is respect. The antidote of respect means to speak to and treat others with the same respect and dignity that one desires for oneself. Respect is about fairness and justice. Interacting with respect reflects a high level of moral conduct and ethical standards, which ultimately leads to being respected by others.

The antidote to the emotion in the category of anger/frustration/lashing out is patience. The antidote of patience is required to learn to control ones anger. Patience does not imply that one should ignore provoking situations. Patience is the antidote for anger in that the skill of patience will enable a person to take the time to clearly think through how one can best respond in a manner that will serve to promote a peaceful and harmonious resolution.

The antidote to the emotions in the category of extreme need for pleasure/lust is self-discipline. A discipline is a training that is expected to produce a specific character pattern or behavior. Discipline can be a training that produces a moral or mental improvement. Discipline leads to control over behavior in a systematic method. Self-discipline is to make a "discipline" of oneself. One is one's own teacher, trainer, coach, and "disciplinarian". Self-discipline brings self-control through a strong desire for self-control.

The Antidote to the emotions in the category of unwilling to accept responsibility/sloth is responsibility. The antidote of responsibility means to be answerable and accountable for oneself, one's actions, and one's life. The antidote of responsibility requires that a person be willing to view their life from the perspective that we each are ultimately responsible for creating everything that happens. This level of responsibility does not allow for blaming others. When something inadvertent happens one must ask oneself "what is it about me that has contributed to this problem?", "How can I learn and grow from this experience?".

The antidote to the emotions in the category of complaining/gluttony is charity. The antidote of charity is learning to focus less on ourselves and more on others. Charity is more than being philanthropic, it is being caring, giving, and kind. Being charitable is characterized by an attitude of gratefulness, so much so that one desires to share of oneself, one's wealth, or one's learning for the betterment of others. Ultimately when one has gained the ability to be giving of themselves, they experience meaning in their own life.

The antidote to the emotions in the category of envy/jealously/resentment is trust in the Divine. The emotion that results from trusting in Divine (or trusting in God) can be elicited through statements such as; "I have all that I need", and "Everything for a reason". Trust in Divine does not mean that one is not responsible for their lives. Trust means that we may not be able to see why something has happened, but God always has our best interest in mind.

The systems and methods of this invention incorporate the idea of the listed moral concepts as antidotes to negative emotions. Because, body, mind, and spirit health is a dynamic state that requires personal responsibility to develop, learn, grow, mature, and evolve, using these moral concepts or antidotes, the antidotes outline skills for developing virtuous behavior that will fulfill the identified spiritual need(s).

It should be appreciated that the specific negative emotions, spiritual needs, and antidotes outlined herein are for basic explanation and understanding of the systems and methods for improving emotional awareness and self-mastery of this invention. Therefore, the specific negative emotions, spiritual needs, and antidotes outlined herein are not to be construed as limiting the systems or methods of this invention. Thus, in various exemplary embodiments, the systems or methods of this invention can be implemented using different or varied negative emotions, spiritual needs, and/or antidotes.

In various exemplary embodiments of the systems and methods of this invention, a mechanism is provided to assist an individual with the identification of negative emotions that were experienced in a given situation. Because negative emotions are rarely experienced one emotion at a time, the systems and methods of this invention allow a user to recognize feelings and emotions by isolating specific emotions and identifying whether those emotions were experienced during a given situation rather than requiring the user to "pull up" and identify what he/she was feeling. Thus, this invention requires an individual to focus on a particular event (a personal experience, life event, personal story, or the like) in which the individual felt one or more negative emotions. Then, the individual must answer an initial, delineating, question regarding the emotions experienced during that event.

The delineating question serves four purposes. First, the delineating question evokes an honest, introspective response from the individual. Second, the delineating question narrows the individual's emotional responses to either the "fight" or the "flight" swing to assist in the identification of the emotions that were experienced. Third, the delineating question directs the flow of the methods of this invention to the appropriate antidote. Fourth, the delineating question weeds out individuals who are not adept enough at the introspective process to be able to utilize the methods of this invention.

In various exemplary embodiments, the delineating question is: "Was the intention behind your emotions to either build yourself up or to tear someone else down?" If, for example, the individual answers the delineating question affirmatively, the individual is asked whether at least one particular negative emotion, from the category of emotions experienced when an individual attempts to seek power (as part of a "fight" response) was experienced during the event. If, on the other hand, the individual answers the delineating question negatively, the individual is asked whether at least one particular negative emotion, from the category of emotions experienced when an individual attempts to "vent off" power (as part of a "flight" response), was experienced during the event.

When the individual has responded to the particular negative emotion(s) presented, the individual is asked the delineating question a second time. The delineating question is asked twice so that the individual has an opportunity to take a deeper, more complete look at the emotions experienced during the particular event. If the individual's second answer to the delineating question is the same as the first answer, the method of this invention can analyze the user's responses. However, if the second answer to the delineating question is different from the first answer, the individual is asked whether at least one particular negative emotion, from the category of emotions not previously explored, was experienced during the event.

For example, if the individual initially responds "yes" to the delineating question, the individual will identify the "fight" emotions in his/her particular response. Then, if the individual again responds "yes" to the delineating question, all of the negative emotions experienced during the event have been explored. In contrast, if the second response to the delineating question is "no", the individual will have an opportunity to identify any "flight" emotions that he/she may have experienced as well.

Through an analysis of the individual's responses, the systems and methods of this invention allow the individual to clearly see all of the discrete emotions they experienced during the specific event. Thus, the "fight" and "flight" responses experienced by the individual, in response to the event, are separated such that the individual's emotions, which are typically mixed together, can be separated, identified, and labeled.

By separating, identifying, and labeling the individual emotions experienced during the event, the systems and methods of this invention identify at least one negative emotion experienced during the event, correlate each identified negative emotion with an underlying spiritual need, and identify at least one antidote to the spiritual need(s) that have been identified. The antidote(s) are then relayed to the individual in the form of at least one virtuous behavior that will fulfill the identified spiritual need(s).

In this manner, negative emotions, as need driven behavior, are viewed as the symptom(s) that identify a deficient or unmet spiritual need. The systems and methods of this invention help to identify a person's deficient spiritual need(s) according to the negative emotion(s) present in a given situation.

The systems and methods of this invention do not change the emotions of the user, but provide the user with the information required to specifically address the emotions they are feeling and provide knowledge of specific virtuous behavior(s), which, if practiced, will effectively change unhealthy emotional habits and eliminate the experience of selected negative emotion(s).

Thus, the systems and methods of this invention provide an introspective tool that will guide a person to the information necessary to make a healthy change.

This invention separately provides a personal tool that allows a person to take responsibility for his/her emotions and integrate antidotes into his/her life in order to gain a healthier state.

This invention separately provides systems and methods that provide a user with a heightened sense of an internal locus of power. Unlike conventional healing, which is often interpreted as healing from an external locus of power in which a physician, a treatment, or a medicine is the source of healing, an internal locus of power focuses on the belief that the body contains the homeostatic mechanism for self-healing, and a healer or a medicine serves merely to activate the body's own healing process.

In various exemplary embodiments, the systems and methods of this invention foster improved physical, mental, spiritual, and emotional health by providing an "electronic mentor" to assist an individual in their cognitive processing of negative emotions. In these various exemplary embodiments, a software program is installed on, for example a computer, a Personal Digital Assistant (PDA), or a network.

Alternatively, the systems and methods of this invention can be used by a healthcare service provider or an individual as part of a "self-help" program to assist an individual in the cognitive processing of negative emotions.

This invention separately provides systems and methods that combine the mind, body, and spirit principles of a holistic model with the predictability and reproducibility of the allopathic model in an improved "wholistic" approach to health and healing.

This invention separately provides a tool to educate individuals as to the unmet needs that must be addressed in order to improve individual levels of physical, mental, spiritual, and emotional health.

This invention separately provides systems and methods that address the psychological, social, and environmental aspects of illness.

This invention separately provides systems and methods that identify virtuous behaviors that serve as antidotes for negative emotions.

This invention separately provides systems and methods that help individuals acquire the skills necessary to manage their emotions.

This invention separately provides a tool that addresses emotional habits in one's personality, then offers the appropriate antidote (virtue) that will lead to the elimination of the unhealthy emotional habit and to a healthier mind, body, spirit state.

This invention separately provides systems and methods that are designed to complement allopathic medical treatments as healthcare moves towards an integration of allopathic and wholistic healthcare.

This invention separately provides systems and methods that allow individuals to actively participate in personal health promotion.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein:

FIG. 1 shows a chart outlining one exemplary embodiment of an interrelationship between negative emotions, spiritual needs, and antidotes to the negative emotions according to this invention;

DETAILED DESCRIPTION OF THE PREFERRED EMBODIMENT

For simplicity and clarification, the operating principles, design factors, and layout of the systems and methods for processing negative emotions according to this invention are explained with reference to various exemplary embodiments of the systems and methods for processing negative emotions according to this invention. The basic explanation of the operation of the systems and methods for processing negative emotions is applicable for the understanding and design of the constituent components employed in the systems and methods for processing negative emotions of this invention.

Furthermore, for the sake of simplicity, the terms user and/or individual will be used. It should be understood that the terms user and/or individual are not limited to an individual user processing his or her own negative emotions, but can also include anyone using the systems and methods of this invention to assist another in the processing of negative emotions.

Additionally, it should be understood that although the various exemplary embodiments described herein are described with reference to exemplary methods being in the form of a software program, the systems and methods of this invention can be used in a manner that is separate and apart from the software program, such as, for example, utilizing a printed copy of the methods for processing negative emotions according to this invention.

FIG. 1 shows a chart 100 outlining one exemplary embodiment of an interrelationship between negative emotions, spiritual needs, and antidotes to the negative emotions according to this invention, as described above.

Figure 2:
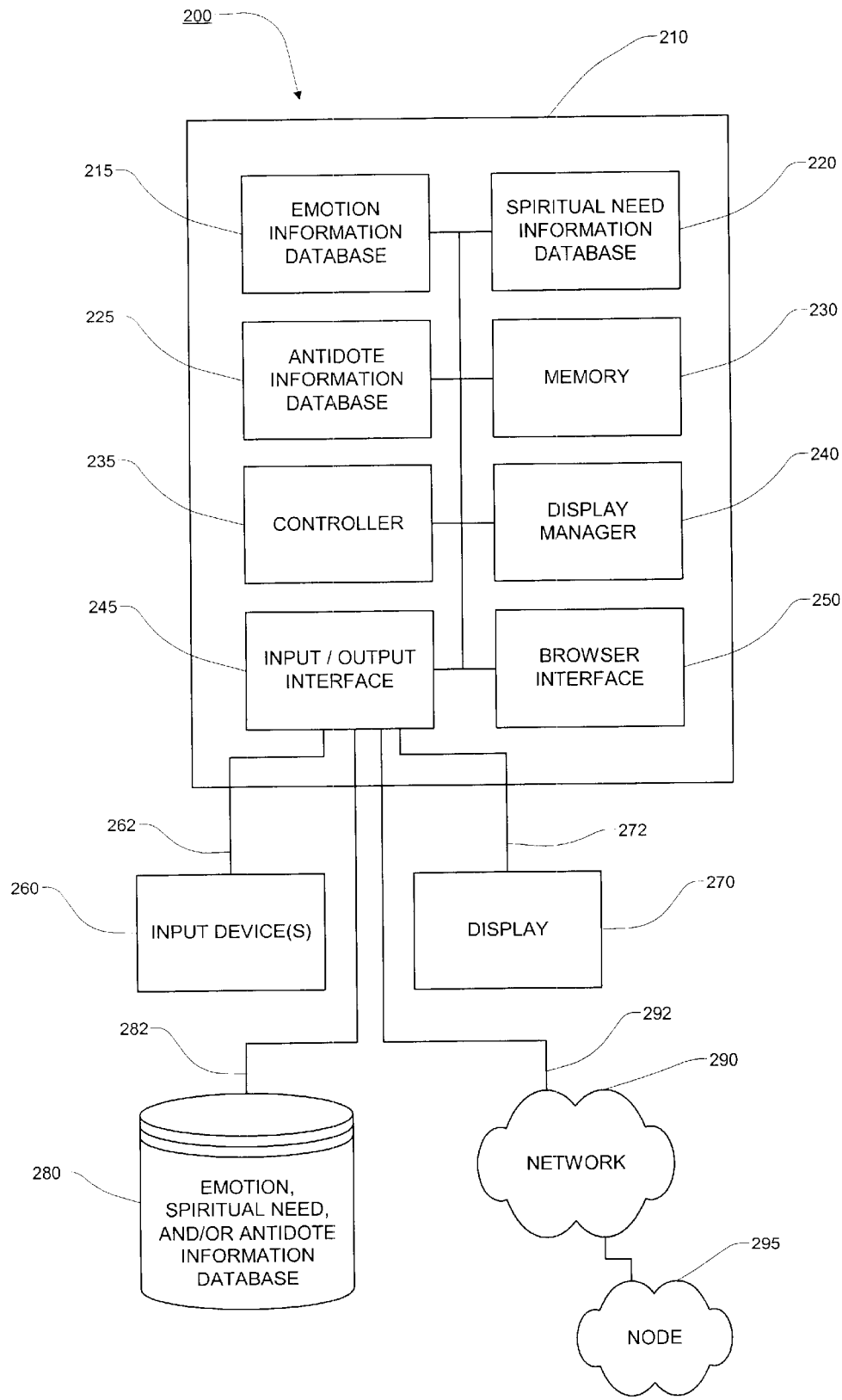
FIG. 2 is a functional block diagram outlining a first exemplary embodiment of a system for improving emotional awareness and self-mastery according to this invention.

FIG. 2 is a functional block diagram outlining a first exemplary embodiment of a system for improving emotional awareness and self-mastery 200 according to this invention. As shown in FIG. 2, the system for improving emotional awareness and self-mastery 200 includes a computer or personal digital assistant (PDA) 210.

The computer or PDA 210 includes at least some of an emotion information database 215, a spiritual need information database 220, an antidote information database 225, a memory 230, a controller 235, a display manager 240, an input/output interface 245, and a browser interface 250. The input/output interface 245 is able to interface with one or more input/output devices 260, a display 270, an emotion, spiritual need, and/or antidote information database 280, and/or a network 290. The input/output interface 245 can also interface with a particular node 295, such as, for example, a specific web page, of the network 290.

As shown in FIG. 2, the emotion information database 215, the spiritual need information database 220, the antidote information database 225, and the memory 230 can be implemented, individually, separately, or as complimentary components, using any appropriate combination of alterable, volatile, non-volatile, non-alterable, or fixed, memory. The alterable memory, whether volatile or non-volatile, can be implemented using any one or more of non-selectable or dynamic RAM, a floppy disk and disk drive, a writable or re-rewriteable optical disk and disk drive, a hard drive, flash memory or the like. Similarly, the non-alterable or fixed memory can be implemented using any one or more of ROM, PROM, EPROM, EEPROM, an optical ROM disk, such as a CD-ROM or DVD-ROM disk, and disk drive or the like.

In various exemplary embodiments, the emotion information database 215, the spiritual need information database 220, the antidote information database 225, and/or the memory 230 store software and data used by the system for improving emotional awareness and self-mastery 200. For example, the emotion information database 215 may store information regarding the negative emotions described herein. The spiritual need information database 220 may store information regarding the spiritual needs and their relation to the negative emotions, as described herein. Additionally, the antidote information database 225 may store information regarding the antidotes and their relation to the negative emotions and/or the spiritual needs, as described herein. Furthermore, the memory 230 may store word processing and communication software.

The controller 235 manages reading data from and writing data to the emotion information database 215, the spiritual need information database 220, the antidote information database 225, and/or the memory 230. The controller 235 also drives the transmission of data to and the reception of data from the input/output devices 260, the display 270, the emotion, spiritual need, and/or antidote information database 280, and/or the network 290, through the input/output interface 245.

The browser interface 250 allows the user to access, through the input/output interface 245, information, including downloadable information, on the network 290 or a particular node 295 of the network 290.

Thus, in various exemplary embodiments, the computer or PDA 210 is able to access, store, retrieve, and process information from any one or more of the emotion information database 215, the spiritual need information database 220, the antidote information database 225, the memory 230, the input/output devices 260, the emotion, spiritual need, and/or antidote information database 280, the network 290, and/or a particular node 295 of the network 290. In this manner, it is not essential that the emotion, spiritual need, or antidote information be stored in the emotion information database 215, the spiritual need information database 220, or the antidote information database 225. Alternatively, this information can be stored in the emotion, spiritual need, and/or antidote information database 280, the network 290, and/or a particular node 295 of the network 290.

In various exemplary embodiments, the system for improving emotional awareness and self-mastery 200 will be included as part of the software executing on a server. It should be appreciated that any other known or later developed system capable of processing and outputting data could be used in place of the server.

In various exemplary embodiments, the computer or PDA 210 also includes a display 270 and one or more input devices 260. In various exemplary embodiments, the display 270 can be a cathode ray tube display, a liquid crystal display, or any other known or later developed system capable of displaying data. In various exemplary embodiments, the display manager 240 drives the display 270. The one or more input devices 260 can be one or more of a keyboard, a mouse, a touch screen, a touch pad, a microphone or any other known or later developed device capable of inputting data.

In the various exemplary embodiments described herein, the computer or PDA 210 interfaces, for example, with one or more input devices 260, the display 270, the emotion, spiritual need, and/or antidote information database 280, the network 290, or a particular node 295 of the network 290, through direct wired connections, via the input/output interface 245.

Alternatively, the computer or PDA 210 can interface with one or more input devices 260, the display 270, the emotion, spiritual need, and/or antidote information database 280, the network 290, or a particular node 295 of the network 290, through any linked connection(s) 262, 272, 282, and 292, respectively. The linked connection(s) 262, 272, 282, and 292 can be any known or later developed device or system for connecting the computer or PDA 210 to the one or more input devices 260, the display 270, the emotion, spiritual need, and/or antidote information database 280, the network 290, or a particular node 295 of the network 290, including a wireless link, a connection over a LAN, a WAN, or any other distributed network, a connection over the public switched telephone network, a connection over a coaxial cable (i.e., CATV) system, a connection over a cellular telephone network, a satellite connection or the like. In general, the linked connection(s) 262, 272, 282, and 292 can be any known or later developed connection system or structure usable to connect the computer or PDA 210 to the one or more input devices 260, the display 270, the emotion, spiritual need, and/or antidote information database 280, the network 290, or a particular node 295 of the network 290, including both wired and wireless connections.

During operation of one exemplary embodiment of the system for improving emotional awareness and self-mastery 200, a user must focus on a particular event (a personal experience, life event, personal story, or the like) in which the individual felt one or more negative emotions. Then, the individual must answer at least one delineating question as further described herein. The delineating question may, for example, be stored in the memory 230 and displayed to the user on the display 270.

The user may respond to the delineating question using on of the input devices 260. In response to the user's initial answer, the system for improving emotional awareness and self-mastery 200 presents at least one negative emotion to the user. The at least one negative emotion may be retrieved from, for example, the emotion information database 215, the emotion, spiritual need, and/or antidote information database 280, the network 290, or the particular node 295 of the network 290 and displayed on the display 270.

The user must then determine whether that particular emotion was experienced during the particular event being analyzed. The user's response can be stored, for example, in the emotion information database 215, the emotion, spiritual need, and/or antidote information database 280, the network 290, or the particular node 295 of the network 290. Once the user responds to the at least one negative emotion presented, the system for improving emotional awareness and self-mastery 200 presents the delineating question again, as described above.

Depending upon the user's second response to the delineating question, the system for improving emotional awareness and self-mastery 200 may present at least one other negative emotion to the user, as described above. The user must then determine whether that particular emotion was experienced during the particular event being analyzed.

Once the user responds to all of the emotions presented, the system for improving emotional awareness and self-mastery 200 correlates each identified emotion with an underlying spiritual need. The spiritual needs may be accessed from, for example, the spiritual need information database 220, the emotion, spiritual need, and/or antidote information database 280, the network 290, or the particular node 295 of the network 290. When the appropriate spiritual need(s) have been identified, the system for improving emotional awareness and self-mastery 200 identifies at least one antidote to the spiritual need(s) that have been identified. The antidote(s) may be stored and accessed from, for example, the antidote information database 225, the emotion, spiritual need, and/or antidote information database 280, the network 290, or the particular node 295 of the network 290.

The antidote(s) are then relayed to the user via, for example, the display 270.

It should be understood that the actions that can be performed by the system for improving emotional awareness and self-mastery 200 of this invention are not limited to the actions listed above. The system for improving emotional awareness and self-mastery 200 of this invention can perform any actions that can be performed by software executing on a programmed general purpose computer, a special purpose computer, a microprocessor, or the like. Furthermore, it should be understood that, the system for improving emotional awareness and self-mastery 200 of this invention can be included as part of the software executing on a server and can be utilized via, for example, an accessed web page.

Figure 3A:
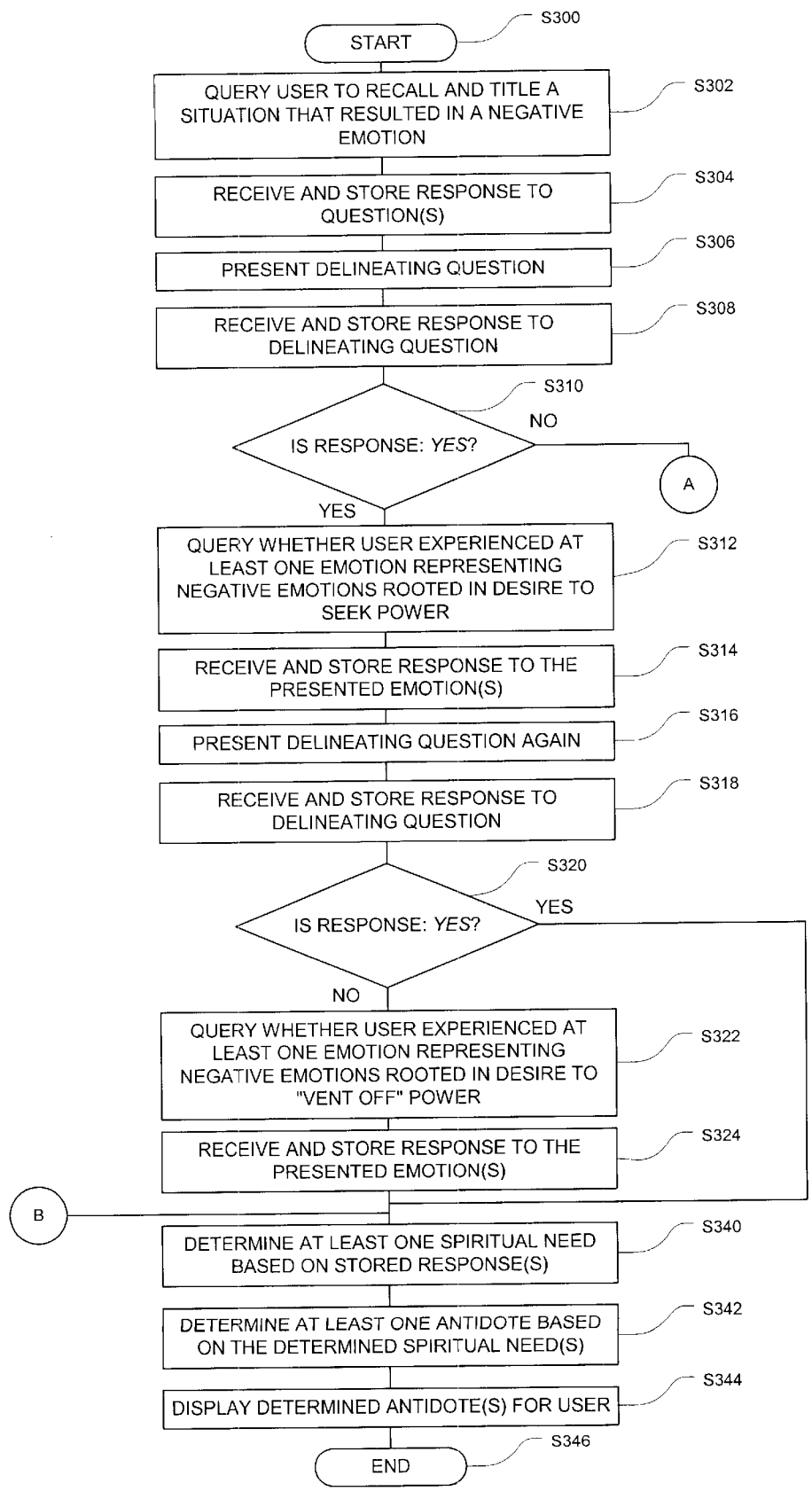
FIGS. 3A and 3B are a flowchart outlining one exemplary embodiment of a method for processing negative emotions according to this invention.
Figure 3B:
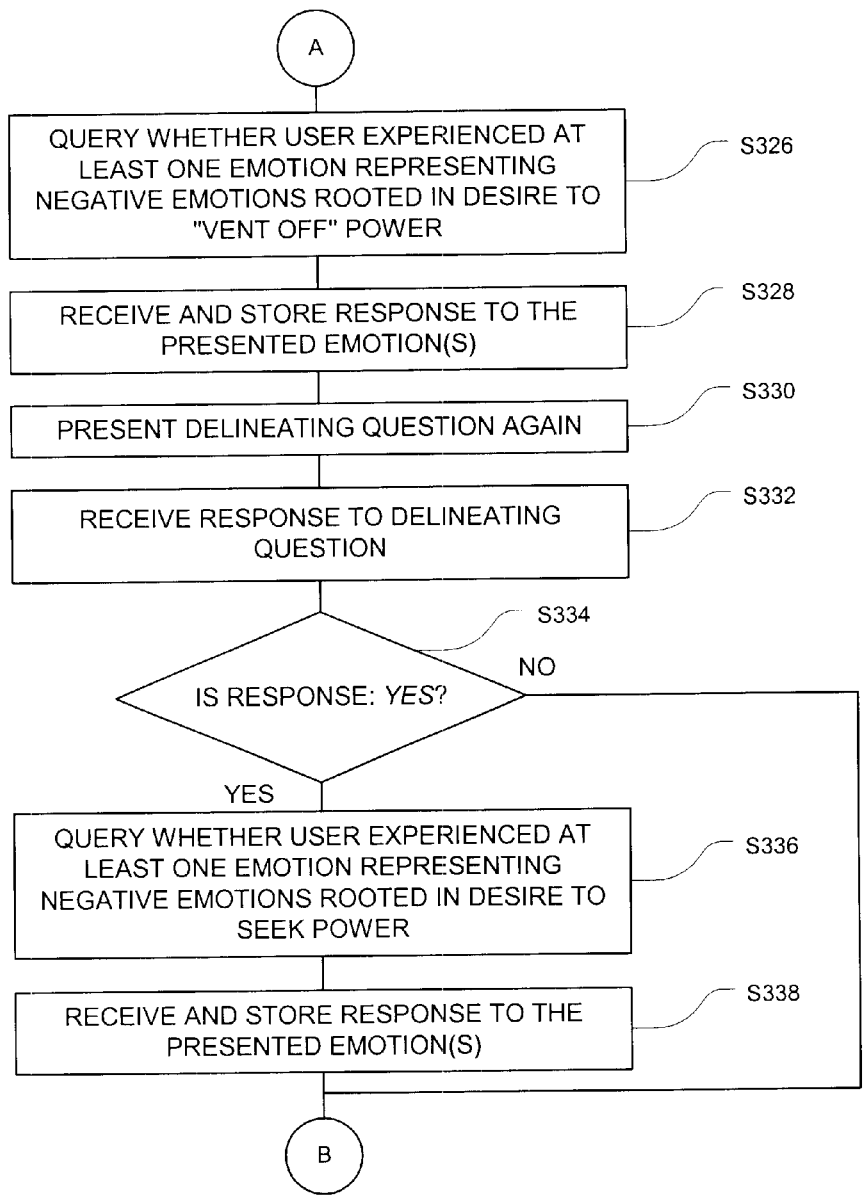

FIGS. 3A and 3B are a flowchart outlining one exemplary embodiment of a method for processing negative emotions according to this invention. As shown in FIG. 3, beginning in step S300, control continues to step S302, where a user is asked to bring to mind an event or situation in which they experienced at least one negative emotion and enter a situation title to enable the user to re-access the information generated at a later date if they so desire.

It should be understood that in various exemplary embodiments, the user may be asked to enter a user name or identification number so that individual user progress and/or multiple user responses can be monitored and/or tracked. In various exemplary embodiments, the user may enter a previously stored situation title, user name, or identification number to access and complete, review, and/or reassess a previously entered situation.

Optionally, step S302 may include providing a "help" option that assists the user in selecting an appropriate title or situation to process. In various exemplary embodiments, the "help" option is a "more information" option that can be selected if the user is having difficulty selecting a situation or titling the chosen situation.

Then, in step S304, the entered situation title, user name, or identification number is stored in a memory. Control then advances to step S306.

In step S306, a delineating question is presented to the user. The delineating question typically requires a "yes" or "no" response. In various exemplary embodiments, the delineating question is: "Was the intention behind your emotions to either build yourself up or to tear someone else down?"

Optionally, step S306 may also include providing a "help" option that assists the user in understanding the delineating question. In various exemplary embodiments, the "help" option is a statement explaining the delineating question, such as, for example, "The delineating question is asking you to look at your intention(s) during the situation that you have chosen. Intention is the aim that guides your feelings and what your emotion was meant to convey. To identify your intention, you must evaluate what you really wanted in the situation."

Then, in step S308, the user's response to the delineating question is received and stored in a memory. Control then advances to step S310.

In step S310 a determination is made whether the user responded "yes" to the delineating question. If, in step S310, it is determined that the user responded "yes" to the delineating question, control continues to step S312. Otherwise, control advances to step S326.

In step S312, at least one negative "fight" emotion rooted in a desire to seek power is presented to the user. The at least one emotion represents an emotion from the group associated with "fight" emotions, described above. When the at least one "fight" emotion is presented, the user is given the opportunity to respond with a "yes" or "no" as to whether that particular emotion was experienced during the situation being processed. Then, in step S314, the user's response to the at least one "fight" emotion is received and stored.

In various exemplary embodiments, the user is sequentially presented with each of the seven negative "fight" emotions, described above. In this manner, when the user responds to a first presented negative "fight" emotion, the response is stored and a second negative "fight" emotion is presented. This routine of steps S312 and S314 is repeated until responses for all seven of the negative "fight" emotions are received and stored.

Then, in step S316, a delineating question is presented to the user. In various exemplary embodiments, the delineating question is the delineating question from step S306 presented to the user a second time.

Optionally, step S316 may also include providing a "help" option that assists the user in understanding why the delineating question is being presented a second time. In various exemplary embodiments, the "help" option is, for example, an information box explaining the purpose of repeating the delineating question, such as, for example, "In the situation being processed, you have already identified the "fight" emotions in the "fight or flight" response. The purpose of asking the delineating question again is to help you take a deeper look at the emotions you were experiencing to determine whether you were also experiencing some aspect of the "flight" response."

Then, in step S318, the user's response to the delineating question is received and stored in a memory. Control then advances to step S320.

In step S320 a determination is made whether the user responded "yes" to the delineating question. If, in step S320, it is determined that the user again responded "yes" to the delineating question, control jumps to step S340. Otherwise, control advances to step S322.

In step S322, at least one negative "flight" emotion rooted in a desire to vent off power is presented to the user. The at least one emotion represents an emotion from the group associated with "flight" emotions, described above. When the at least one "flight" emotion is presented, the user is given the opportunity to respond with a "yes" or "no" as to whether that particular emotion was experienced during the situation being processed. Then, in step S324, the user's response to the at least one "flight" emotion is received and stored.

In various exemplary embodiments, the user is sequentially presented with each of the seven negative "fight" emotions, described above. In this manner, when the user responds to a first presented negative "flight" emotion, the response is stored and a second negative "flight" emotion is presented. This routine of steps S322 and S324 is repeated until responses for all seven of the negative "flight" emotions are received and stored.

If, in step S310, it was determined that that the user responded "no" to the delineating question, as initially presented, control continues to step S326. In step S326, at least one negative "flight" emotion rooted in a desire to vent off power is presented to the user. The at least one emotion represents an emotion from the group associated with "flight" emotions, described above. When the at least one "flight" emotion is presented, the user is given the opportunity to respond with a "yes" or "no" as to whether that particular emotion was experienced during the situation being processed. Then, in step S328, the user's response to the at least one "flight" emotion is received and stored.

In various exemplary embodiments, the user is sequentially presented with each of the seven negative "fight" emotions, described above. In this manner, when the user responds to a first presented negative "flight" emotion, the response is stored and a second negative "flight" emotion is presented. This routine of steps S326 and S328 is repeated until responses for all seven of the negative "flight" emotions are received and stored.

Next, in step S330, a delineating question is presented to the user. In various exemplary embodiments, the delineating question is the delineating question from step S306 presented to the user a second time.

Optionally, step S330 may also include providing a "help" option that assists the user in understanding why the delineating question is being presented a second time. In various exemplary embodiments, the "help" option is, for example, an information box explaining the purpose of repeating the delineating question, such as, for example, "In the situation being processed, you have already identified the "flight" emotions in the "fight or flight" response. The purpose of asking the delineating question again is to help you take a deeper look at the emotions you were experiencing to determine whether you were also experiencing some aspect of the "fight" response."

Then, in step S332, the user's response to the delineating question is received and stored in a memory. Control then advances to step S334.

In step S334 a determination is made whether the user responded "yes" to the delineating question. If, in step S334, it is determined that the user responded "no" to the delineating question, control jumps to step S340. Otherwise, control advances to step S336.

In step S336, at least one negative "fight" emotion rooted in a desire to seek power is presented to the user. The at least one emotion represents an emotion from the group associated with "fight" emotions, described above. When the at least one "fight" emotion is presented, the user is given the opportunity to respond with a "yes" or "no" as to whether that particular emotion was experienced during the situation being processed. Then, in step S338, the user's response to the at least one "fight" emotion is received and stored.

In various exemplary embodiments, the user is sequentially presented with each of the seven negative "fight" emotions, described above. In this manner, when the user responds to a first presented negative "fight" emotion, the response is stored and a second negative "fight" emotion is presented. This routine of steps S336 and S338 is repeated until responses for all seven of the negative "fight" emotions are received and stored. Control then continues to step S340.

In step S340, at least one appropriate spiritual need is determined based on the stored user response(s) to the negative "flight" and "fight" emotion(s) presented. In various exemplary embodiments, the determined spiritual need(s) is/are displayed for the user. Then, in step S342, at least one appropriate antidote is determined based on the determined spiritual needs.

Control then continues to step S344, where the at least one determined antidote is displayed for the user. Then, in step S340, the method ends.

It should be understood that in each step that requires a response from the user, as described above, the user is able to abort the program and automatically end the method. For example, if the user is unable to understand or answer the delineating question, if the user cannot determine his or her intentions, or if the user cannot grasp the significance of responding to the presented emotion(s), the user may choose to abort the program.

Figure 4:
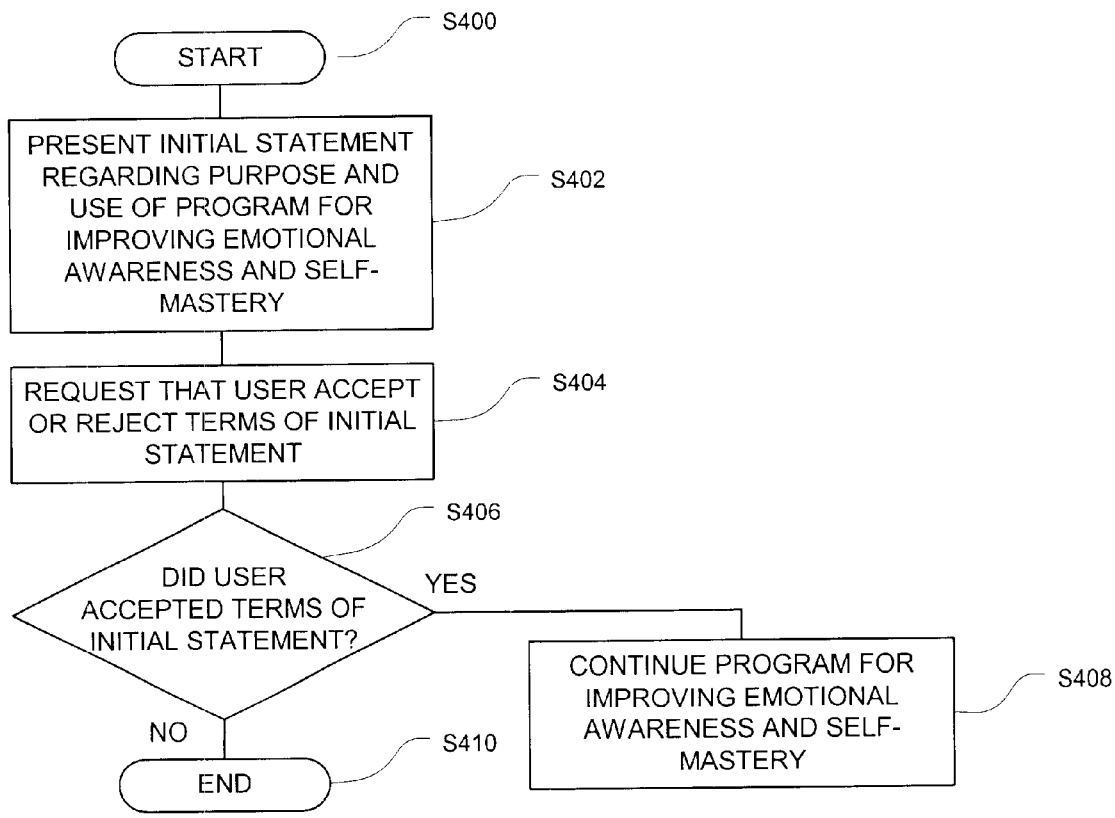
FIG. 4 is a flowchart outlining one exemplary embodiment of optional steps usable in conjunction with the flowchart of FIGS. 3A and 3B.

FIG. 4 is a flowchart outlining one exemplary embodiment of optional steps usable in conjunction with the flowchart of FIGS. 3A and 3B. It should be appreciated that the optional steps S400–S410, as shown in FIG. 4, can be utilized at any point in the flowchart of FIGS. 3A and 3B. However, optional steps S400–S410 preferably appear as preliminary steps, for example before step S302 of FIG. 3A.

As shown in FIG. 4, beginning in step S400, control continues to step S402, where the user is presented with an initial statement regarding the purpose and use of the program for improving emotional awareness and self-mastery according to this invention. In various exemplary embodiments, the initial statement is:

"This program for improving emotional awareness and self-mastery is a tool based on a premise of personal responsibility for health and wellness. Personal responsibility is a preliminary requirement for the acquisition and/or maintenance of health and well being. This program for improving emotional awareness and self-mastery is a tool that is designed so that it can be self-administered. It is not necessary to evoke the assistance of a Psychotherapist, Psychiatrist, or other mental health provider to utilize this tool.

The issue being addressed in this screen is intended to clearly state that each individual is responsible for the decisions they make in their lives. This program for improving emotional awareness and self-mastery does not implement treatments or make life changes for you, it merely provides the necessary information regarding the unmet need(s) that are present in your life, and the antidote(s) that will alter your experience of emotion(s) and hence fill your deficient need(s)."

Then, in step S404, the user is requested to either accept or reject the terms of the initial statement. Control then continues to step S406.

In step S406, a determination is made whether the user accepted or rejected the terms of the initial statement.

If in step S406, it is determined that the user accepted the terms of the initial statement, control continues to step S408 and the program for improving emotional awareness and self-mastery is continued. Otherwise, control advances to step S410 where the program for improving emotional awareness and self-mastery is aborted and the method ends.

Figure 5:
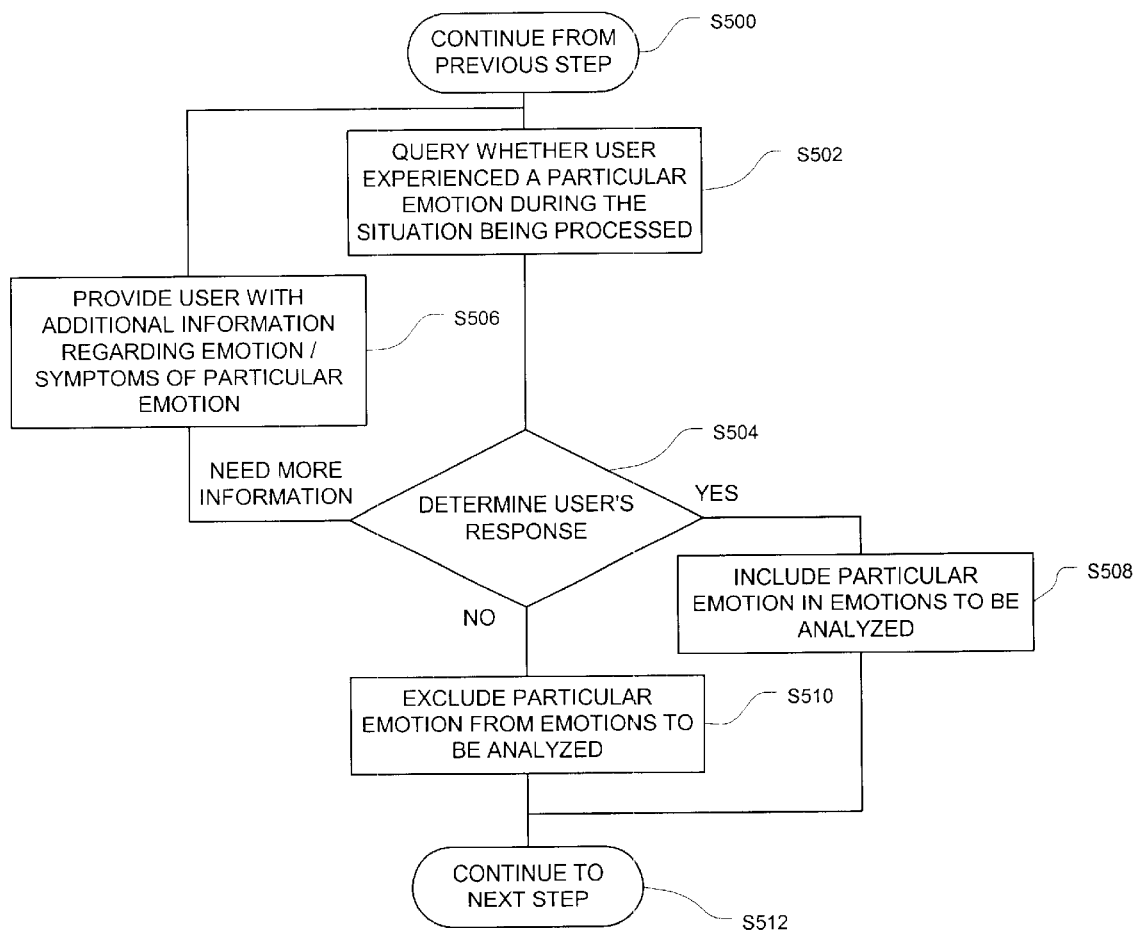
FIG. 5 is a flowchart outlining one exemplary embodiment of additional steps usable in conjunction with the flowchart of FIGS. 3A and 3B.

FIG. 5 is a flowchart outlining one exemplary embodiment of additional steps usable in conjunction with the flowchart of FIGS. 3A and 3B. It should be appreciated that the optional steps S500–S512, as shown in FIG. 5, can be utilized at any point in the flowchart of FIGS. 3A and 3B. However, optional steps S500–S512 preferably appear as a replacement for any step that requires the user to identify a particular emotion experienced during the situation being processed. For example, the optional steps S500–S512 may replace steps S312 and S314, S322 and S324, S326 and S328, and/or S336 and S338 of FIGS. 3A and 3B.

As shown in FIG. 5, beginning in step S500, control continues to step S502, where the user is presented with a particular emotion and given the opportunity to determine whether that particular emotion was experienced during the situation being processed. This is similar to the steps S312, S322, S326, and/or S336 of FIGS. 3A and 3B.

However, as shown in FIG. 5, the user is able to respond with a "yes", a "no", or a "Show me more information on the particular emotion and/or the symptoms of the particular emotion." Control then advances to step S504.

In step S504 a determination is made whether the user responded "yes", "no", or "Show me more information". If, in step S504, it is determined that the user responded "Show me more information", control continues to step S506 where the user is provided with additional information on the particular emotion and/or the symptoms of the particular emotion. Control then returns to step S502 and the user is given the opportunity to determine whether that particular emotion was experienced during the situation being processed.

If, in step S504, it is determined that the user responded "yes", control advances to step S508, where the particular emotion is stored as one of the emotions to be analyzed. Control then advances to step S512.

If, in step S504, it is determined that the user responded "no", control jumps to step S510, where the particular emotion is excluded from the emotions to be analyzed. Control then advances to step S512.

In step S512, the method continues using the emotion(s) identified by the user as being experienced during the situation being processed.

It should be understood that steps S500–S512 may be utilized to sequentially present one or more negative emotions to the user.

It should be appreciated that each of the elements of the system for improving emotional awareness and self-mastery 200 shown in FIG. 2 can be implemented as portions of a suitably programmed general purpose computer. Alternatively, each of the elements of the system for improving emotional awareness and self-mastery 200 shown in FIG. 2 can be implemented as physically distinct hardware circuits within an ASIC, or using a FPGA, a PDL, a PLA or a PAL, or using discrete logic elements or discrete circuit elements. The particular form that each of the elements of the system for improving emotional awareness and self-mastery 200 shown in FIG. 2 will take is a design choice and will be obvious and predicable to those skilled in the art.

Moreover, the systems and methods for improving emotional awareness and self-mastery can be implemented as software executing on a programmed general-purpose computer, a special purpose computer, a microprocessor, or the like. In various exemplary embodiments, the systems and methods for improving emotional awareness and self-mastery can be implemented as a routine embedded in a network client, as a resource residing on a network server, or the like. The systems and methods for improving emotional awareness and self-mastery can also be implemented by physically incorporating them into a software and/or hardware system, such as the hardware or firmware systems of another personal digital assistant, bidirectional pager, analog or digital cellular telephone, or the like.

Thus, in summary, the systems and methods for improving emotional awareness and self-mastery can be implemented on a programmed general purpose computer, a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowcharts shown in FIGS. 3A, 3B, 4, and/or 5, can be used to implement the systems and methods for improving emotional awareness and self-mastery.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method for providing an individual with improved emotional awareness and self-mastery, comprising the steps of:

asking an individual to recall a situation in which at least one negative emotion was experienced;

determining whether the individual's emotional responses to the recalled situation included "fight" emotions or "flight" emotions;

presenting, if the individual's emotional responses to the recalled situation included "fight" emotions, at least one "fight" emotion to the individual and asking the individual to determine whether he/she experienced the at least one "fight" emotion during the recalled situation;

presenting, if the individual's emotional responses to the recalled situation included "flight" emotions, at least one "flight" emotion to the individual and asking the individual to determine whether he/she experienced the at least one "flight" emotion during the recalled situation;

presenting, if the individual's emotional responses to the recalled situation included both "fight" and "flight" emotions, at least one "fight" emotion and at least one "flight" emotion to the individual and asking the individual to determine whether he/she experienced the at least one "fight" emotion and/or the at least one "flight" emotion during the recalled situation;

associating any identified "fight" and/or "flight" emotion(s) the individual experienced during the recalled situation with at least one predetermined spiritual need, such that each identified "fight" and/or "flight" emotion corresponds to a single, predetermined spiritual need;

identifying, based on each associated, predetermined spiritual need, at least one predetermined antidote to counter each identified "fight" and/or "flight" emotion; and presenting the at least one identified, predetermined antidote to the individual.

2. The method of claim 1, wherein each predetermined spiritual need is from the group of community, honor, love, joy, life lessons, life work, and faith.

3. The method of claim 2, wherein the "fight" emotions include at least one from the group of pride, extreme desire, anger/frustration/lashing out, extreme need for pleasure, unwillingness to accept responsibility, complaining, and envy/jealousy/resentment.

4. The method of claim 3, wherein:
the "fight" emotion of pride is associated with the predetermined spiritual need for community;
the "fight" emotion of extreme desire is associated with the predetermined spiritual need for honor;
the "fight" emotion of anger/frustration/lashing out is associated with the predetermined spiritual need for love;
the "fight" emotion of extreme need for pleasure is associated with the predetermined spiritual need for joy;
the "fight" emotion of unwillingness to accept responsibility is associated with the predetermined spiritual need for life lessons;
the "fight" emotion of complaining is associated with the predetermined spiritual need for life work; and
the "fight" emotion of envy/jealousy/resentment is associated with the predetermined spiritual need for faith.

5. The method of claim 4, wherein each predetermined spiritual need associated with a "fight" emotion has a predetermined antidote, such that:
the predetermined spiritual need for community is associated with a predetermined antidote of humility;
the predetermined spiritual need for honor is associated with a predetermined antidote of respect;
the predetermined spiritual need for love is associated with a predetermined antidote of patience;
the predetermined spiritual need for joy is associated with a predetermined antidote of self-discipline;
the predetermined spiritual need for life lessons is associated with a predetermined antidote of responsibility;
the predetermined spiritual need for life work is associated with a predetermined antidote of charity; and
the predetermined spiritual need for faith is associated with a predetermined antidote of trust in Divine.

6. The method of claim 2, wherein the "flight" emotions include at least one from the group of lonely, guilt/shame, hurt feelings/loss, blue/down, hopeless/helpless/victimized, dissatisfied/worthless, and anxiousness/worry/stress.

7. The method of claim 6, wherein:
a "flight" emotion of lonely is associated with the predetermined spiritual need for community;
a "flight" emotion of guilt/shame is associated with the predetermined spiritual need for honor;
a "flight" emotion of hurt feelings/loss is associated with the predetermined spiritual need for love;
a "flight" emotion of blue/down is associated with the predetermined spiritual need for joy;
a "flight" emotion of hopeless/helpless/victimized is associated with the predetermined spiritual need for life lessons;
a "flight" emotion of dissatisfied/worthless is associated with the predetermined spiritual need for life work; and
a "flight" emotion of anxiousness/worry/stress is associated with the predetermined spiritual need for faith.

8. The method of claim 7, wherein each predetermined spiritual need associated with a "flight" emotion has a predetermined antidote, such that:
the predetermined spiritual need for community is associated with a predetermined antidote of friendship;
the predetermined spiritual need for honor is associated with a predetermined antidote of courage;
the predetermined spiritual need for love is associated with a predetermined antidote of compassion;
the predetermined spiritual need for joy is associated with a predetermined antidote of present living;
the predetermined spiritual need for life lessons is associated with a predetermined antidote of responsibility;
the predetermined spiritual need for life work is associated with a predetermined antidote of perseverance; and
the predetermined spiritual need for faith is associated with a predetermined antidote of trust in Divine.

9. The method of claim 1, wherein the step of determining whether the individual's emotional responses to the recalled situation included either "fight" emotions or "flight" emotions includes presenting a delineating question to the individual to assist in the identification of emotions that were experienced during the recalled situation.

10. The method of claim 9, wherein the delineating question requires a "yes" or "no" response.

11. The method of claim 9, further including the step of presenting a second delineating question to the individual to assist in the identification of emotions that were experienced during the recalled situation.

12. The method of claim 11, wherein the second delineating question is the same question used as the first delineating question, such that the delineating question is repeated as the second delineating question.

13. The method of claim 1, further including the step of providing the individual with instructions on how to select an appropriate situation in which at least one negative emotion was experienced.

14. The method of claim 1, further including the step of providing the individual with a definition of the at least one "fight" emotion, the at least one "flight" emotion, the predetermined spiritual need, and/or the at least one predetermined antidote presented to the individual.

15. The method of claim 1, further including the step of providing an abort mechanism that allows the individual to abort the method.

16. A method for improving emotional awareness and self-mastery, comprising the steps of:
   recalling a situation in which at least one negative emotion was experienced;
   determining whether emotional responses to the recalled situation included "fight" emotions or "flight" emotions;
   analyzing, if the emotional responses to the recalled situation included "fight" emotions, at least one "fight" emotion and determining whether the at least one "fight" emotion was experienced during the recalled situation;
   analyzing, if the emotional responses to the recalled situation included "flight" emotions, at least one "flight" emotion and determining whether the at least one "flight" emotion was experienced during the recalled situation;
   analyzing, if the emotional responses to the recalled situation included both "fight" and "flight" emotions, at least one "fight" emotion and at least one "flight" emotion;
   determining whether the at least one "fight" emotion and/or the at least one "flight" emotion was experienced during the recalled situation;
   associating any identified "fight" and/or "flight" emotion(s) experienced during the recalled situation with at least one predetermined spiritual need, such that each identified "fight" and/or "flight" emotion corresponds to a single, predetermined spiritual need;
   identifying, based on each associated, predetermined spiritual need, at least one predetermined antidote to counter each identified "fight" and/or "flight" emotion.

17. A method for determining an antidote to an emotion, comprising the steps of:
   identifying at least one "fight" emotion or "flight" emotion experienced during a particular event;
   correlating the at least one identified "fight" emotion or "flight" emotion to at least one predetermined spiritual need, such that each identified "fight" emotion or "flight" emotion corresponds to a single, predetermined spiritual need;
   identifying, based on each predetermined spiritual need, at least one predetermined antidote to counter each identified "fight" emotion or "flight" emotion; and
   presenting the at least one identified antidote, wherein the at least one identified antidote identifies at least one virtuous behavior.

18. An interactive automatic system for improving emotional awareness and self-mastery, comprising:
   a display device that allows a counselee to view emotion, spiritual need, and/or antidote information;
   a memory that stores accessible emotion, spiritual need, and antidote information, wherein the emotion information includes power-seeking negative emotions and "venting off" negative emotions, and wherein the spiritual need information includes information regarding community, honor, love, joy, life lessons, life work, and faith, and wherein the antidote information includes information regarding friendship, courage, compassion, present living, responsibility, perseverance, trust in Divine, humility, respect, patience, self discipline, and charity, such that at least some of the spiritual need information is correlated to the power-seeking negative emotions and "venting off" negative emotions; and
   an input/output module for interactively evaluating the counselee's emotional awareness and self-mastery and providing antidotes for identified spiritual needs.

19. The interactive automatic system of claim 18, further comprising:
   means for allowing the user to interactively evaluate his/her negative emotions as expressed during a given situation; and
   means responsive to the evaluation of the negative emotions expressed during the given situation for recommending at least one virtuous behavior as an antidote to the negative emotions experienced by the user.

20. The interactive automatic system of claim 18, further comprising a browser interface that allows the user to access emotion, spiritual need, and/or antidote information via a network.

21. The interactive automatic system of claim 18, further comprising a means for allowing a user to store evaluated situations for future reference.

22. A system for determining an antidote to an emotion, comprising:
   means for identifying at least one emotion experienced during a particular event, wherein the at least one emotion is selected from the group comprising power-seeking negative emotions and "venting off" negative emotions;
   means for correlating the at least one identified emotion with at least one spiritual need, wherein the at least one spiritual need is selected from the group comprising community, honor, love, joy, life lessons, life work, and faith;
   means for identifying at least one antidote to the at least one identified spiritual need, wherein the at least one antidote is selected from the group comprising friendship, courage, compassion, present living, responsibility, perseverance, trust in Divine, humility, respect, patience, self discipline, and charity; and
   means for presenting the at least one identified antidote, wherein the at least one identified antidote identifies at least one virtuous behavior.

23. The interactive automatic system of claim 18, wherein the power-seeking negative emotions include pride, extreme desire, anger/frustration/lashing out, extreme need for pleasure, unwillingness to accept responsibility, complaining, and envy/jealousy/resentment, and wherein the "venting off" negative emotions include lonely, guilt/shame, hurt feelings/loss, blue/down, hopeless/helpless/victimized, dissatisfied/worthless, and anxiousness/worry/stress.

24. The system of claim 22, wherein the power-seeking negative emotions include pride, extreme desire, anger/frustration/lashing out, extreme need for pleasure, unwillingness to accept responsibility, complaining, and envy/jealousy/resentment, and wherein the "venting off" negative emotions include lonely, guilt/shame, hurt feelings/loss, blue/down, hopeless/helpless/victimized, dissatisfied/worthless, and anxiousness/worry/stress.

25. An interactive automatic system for improving emotional awareness and self-mastery, comprising:

a display device that allows a counselor to view emotion, spiritual need, and/or antidote information;

a memory that stores accessible emotion, spiritual need, and antidote information, wherein the emotion information includes power-seeking negative emotions and "venting off" negative emotions, and wherein the spiritual need information includes information regarding community, honor, love, joy, life lessons, life work, and faith, and wherein the antidote information includes information regarding friendship, courage, compassion, present living, responsibility, perseverance, trust in Divine, humility, respect, patience, self discipline, and charity, such that at least some of the spiritual need information is correlated to the power-seeking negative emotions and "venting off" negative emotions; and an input/output module for allowing the counselor to interactively evaluate a counselee's emotional awareness and self-mastery and providing the counselor with antidotes for the counselee's identified spiritual needs.

* * * * *